(12) United States Patent
Riechers et al.

(10) Patent No.: US 6,610,691 B1
(45) Date of Patent: *Aug. 26, 2003

(54) CARBOXYLIC ACID DERIVATIVES, THEIR PRODUCTION AND USE

(75) Inventors: Hartmut Riechers, Neustadt (DE); Dagmar Klinge, Heidelberg (DE); Wilhelm Amberg, Friedrichsdorf (DE); Andreas Kling, Mannheim (DE); Heinz Hillen, Hassloch (DE); Liliane Unger, Ludwigshafen (DE); Bernd Elger, Neustadt (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,946

(22) PCT Filed: Apr. 4, 1997

(86) PCT No.: PCT/EP97/01684
§ 371 (c)(1),
(2), (4) Date: Oct. 8, 1998

(87) PCT Pub. No.: WO97/38980
PCT Pub. Date: Oct. 23, 1997

(30) Foreign Application Priority Data

Apr. 12, 1996 (DE) .......................... 196 14 534

(51) Int. Cl.⁷ .................... C07D 239/52; C07D 251/26; A61K 31/505; A61K 31/53; A61P 9/02

(52) U.S. Cl. .................. 514/241; 514/274; 544/315; 544/318; 544/219

(58) Field of Search ................... 514/274, 241; 544/315, 318, 219

(56) References Cited

FOREIGN PATENT DOCUMENTS

| EP | 481 512 | 4/1992 |
|---|---|---|
| HU | P9901315 | 8/1999 |
| WO | WO 94/25442 | 11/1994 |

*Primary Examiner*—Richard L. Raymond
*Assistant Examiner*—Venkataraman Balasubramanian
(74) *Attorney, Agent, or Firm*—Wood, Phillips, Katz, Clark & Mortimer

(57) ABSTRACT

The invention relates to carboxylic acid derivatives of the formula

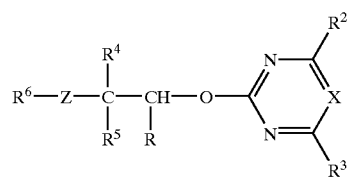

where the radicals have the meanings defined in the description, to the preparation of these compounds and to their use as drugs.

15 Claims, No Drawings

CARBOXYLIC ACID DERIVATIVES, THEIR PRODUCTION AND USE

The present invention relates to new carboxylic acid derivatives, their preparation and use.

Endothelin is a peptide which is composed of 21 amino acids and is synthesized and released by the vascular endothelium. Endothelin exists in three isoforms, ET-1, ET-2 and ET-3. In the following text, "endothelin" or "ET" signifies one or all isoforms of endothelin. Endothelin is a potent vasoconstrictor and has a potent effect on vessel tone. It is known that this vasoconstriction is caused by binding of endothelin to its receptor (Nature, 332, 411–415, 1988; FEBS Letters, 231, 440–444, 1988 and Biochem. Biophys. Res. Commun., 154, 868–875, 1988).

Increased or abnormal release of endothelin causes persistent vasoconstriction in the peripheral, renal and cerebral blood vessels, which may lead to illnesses. It has been reported in the literature that endothelin is involved in a number of illnesses; these include hypertension, myocardial infarct, heart failure, kidney failure, pulmonary hypertension, Raynaud's syndrome, cerebral vasospasms, atherosclerosis, stroke, benign prostate hypertrophy and asthma (Japan J. Hypertension 12, 79 (1989), J. Vascular Med. Biology 2, 207 (1990), J. Am. Med. Association 264, 2868 (1990), Nature 344, 11 (1990), N. Engl. J. Med. 322, 205 (1989), N. Engl. J. Med. 328, 1732 (1993), Nephron 66, 373 (1994), Strake 25, 904 (1994), Nature 365, 759 (1993), J. Mol. Cell. Cardiol. 27, A234 (1995), Cancer Research 56, 663 (1996)).

Accordingly, substances which specifically inhibit the binding of endothelin to the receptor ought also to antagonize the various abovementioned physiological effects of endothelin and therefore be valuable drugs.

The German Patent Application with the file number P 44 36 851.8 describes the following compounds as endothelin receptor antagonists:

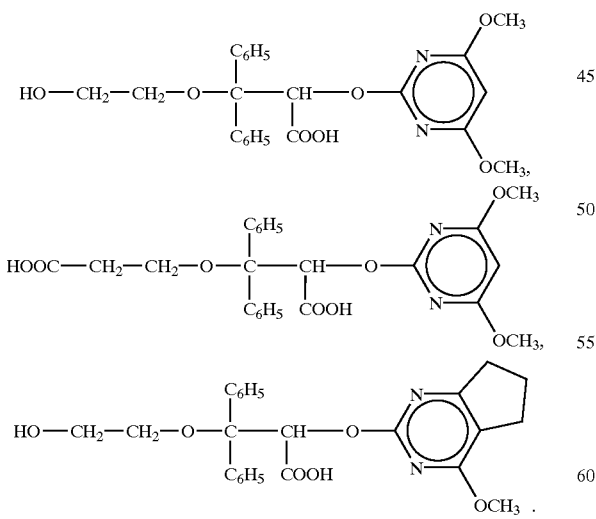

We have now found that certain carboxylic acid derivatives are good inhibitors of endothelin receptors and that these compounds simultaneously have a relatively low plasma binding.

The invention relates to carboxylic acid derivatives of the formula I

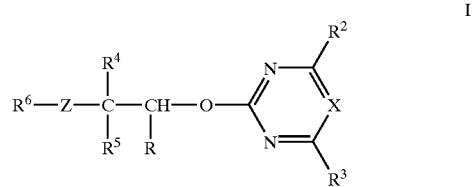

where R is a formyl group, tetrazole [sic], nitrile [sic], a group COOH or a radical which can be hydrolyzed to COOH, and the other substituents have the following meanings:

$R^2$ halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X nitrogen or $CR^{14}$, where $R^{14}$ is hydrogen or $C_{1-5}$-alkyl, or $CR^{14}$ forms together with $CR^3$ a 5- or 6-membered alkylene or alkenylene ring which can be substituted by one or two $C_{1-4}$-alkyl groups and in which in each case one methylene group can be replaced by oxygen, sulfur, —NH or —N$C_{1-4}$-alkyl;

$R^3$ halogen, $C_1$–$C_4$-alkyl, $C_1$–$C_4$-haloalkyl, $C_1$–$C_4$-alkoxy, $C_1$–$C_4$-haloalkoxy, —NH—O—$C_{1-4}$-alkyl, $C_1$–$C_4$-alkylthio or $CR^3$ is linked to $CR^{14}$ as indicated above to form a 5- or 6-membered ring;

$R^4$ and $R^5$ (which may be identical or different):
 phenyl or naphthyl, each of which can be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino, $C_1$–$C_4$-alkylamino or $C_1$–$C_4$-dialkylamino;
 phenyl or naphthyl which are connected together in ortho positions by a direct linkage, a methylene, ethylene or ethenylene group, an oxygen or sulfur atom or an $SO_2$, NH or N-alkyl group, or $C_3$–$C_7$-cycloalkyl;

$R^6$ $C_1$–$C_{10}$-alkyl, $C_3$–$C_{10}$-alkenyl or $C_3$–$C_{10}$-alkynyl, the radicals each being substituted one or more times by hydroxyl, mercapto, carboxy,

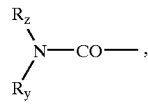

where $R_y$ and $R_z$ are, independently of one another, hydrogen or $C_1$–$C_5$-alkyl; sulfonyl, cyano, guanidino;

Z sulfur or oxygen.

The compounds, and the intermediates for preparing them, eg. IV and VI, may have one or more asymmetrically substituted carbon atoms. Such compounds may exist as pure enantiomers and pure diastereomers or as a mixture thereof. The use of an enantiomerically pure compound as active substance is preferred.

The invention furthermore relates to the use of the abovementioned carboxylic acid derivatives for producing drugs, in particular for producing endothelin-receptor inhibitors.

The compounds according to the invention are prepared starting from the epoxides IV, which are obtained in a conventional way, eg. as described in J. March, Advanced Organic Chemistry, 2nd Ed., 1983, pages 862 and 750 from the ketones II or the olefins III:

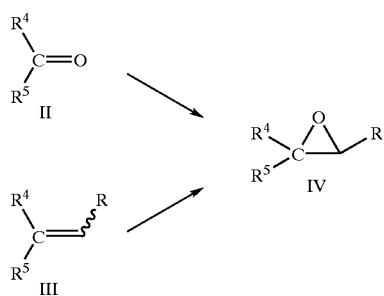

Carboxylic acid derivatives of the general formula VI can be prepared by reacting the epoxides of the general formula IV (eg. with R=ROOR$^{10}$ [sic] with alcohols or thiols of the general formula V where R$^6$ and Z have the meanings stated in claim 1.

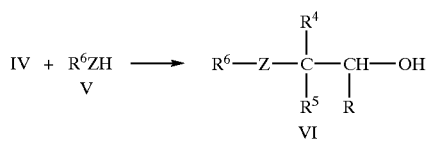

For this purpose, compounds of the general formula IV are heated with a compound of the formula V in the molar ratio of about 1:1 to 1:7, preferably 1 to 3 mol equivalents, at from 50 to 200° C., preferably 80 to 150° C.

Other functional groups in R$^6$ are initially protected in a conventional way for the reaction with compounds of the formula IV; for example, alcohols can be protected as acetates, diols as acetals and carboxyl groups as esters. The protective groups can be eliminated after the reaction of compounds of the formula VI with VII.

The reaction may also take place in the presence of a diluent. It is possible to use for this purpose all solvents which are inert toward the reagents used.

Examples of such solvents or diluents are water, aliphatic, alicyclic and aromatic hydrocarbons, which may in each case be chlorinated, such as hexane, cyclohexane, petroleum ether, naphtha, benzene, toluene, xylene, methylene chloride, chloroform, carbon tetrachloride, ethyl chloride and trichloroethylene, ethers such as diisopropyl ether, dibutyl ether, methyl tert-butyl ether, propylene oxide, dioxane and tetrahydrofuran, ketones such as acetone, methyl ethyl ketone, methyl isopropyl ketone and methyl isobutyl ketone, nitrites such as acetonitrile and propionitrile, alcohols such as methanol, ethanol, isopropanol, butanol and ethylene glycol, esters such as ethyl acetate and amyl acetate, amides such as dimethylformamide and dimethylacetamide, sulfoxides and sulfones, such as dimethyl sulfoxide and sulfolane, bases such as pyridine, N-methylpyrrolidone, cyclic ureas such as 1,3-dimethyl-2-imidazolidinone and 1,3-dimethyl-3,4,5,6-tetra-hydro-2(1H) pyrimidinone.

The reaction is preferably carried out at a temperature in the range from 0° C. to the boiling point of the solvent or mixture of solvents.

The presence of a catalyst may be advantageous. Suitable catalysts in this case are strong organic and inorganic acids, and Lewis acids. Examples thereof are, inter alia, sulfuric acid, hydrochloric acid, trifluoroacetic acid, p-toluenesulfonic acid, boron trifluoride etherate and titanium(IV) alcoholates.

Compounds of the general formula VI can be obtained in enantiomerically pure form by starting from enantiomerically pure compounds of the formula IV and reacting them with compounds of the formula V in the manner described.

It is furthermore possible to obtain enantiomerically pure compounds of the formula VI by carrying out a classical racemate resolution with racemic or diastereomeric compounds of the formula VI using suitable enantiomerically pure bases such as brucine, strychnine, quinine, quinidine, chinchonidine [sic], chinchonine [sic], yohimbine, morphine, dehydroabietylamine, ephedrine (–), (+), deoxyephedrine (+), (–), threo-2-amino-1-(p-nitrophenyl)-1,3-propanediol (+), (–), threo-2-(N,N-dimethylamino)-1-(p-nitrophenyl)-1,3-propanediol (+), (–), threo-2-amino-1-phenyl-1,3-propanediol (+), (–), α-methylbenzylamine (+), (–), α-(1-naphthyl)ethylamine (+), (–), α-(2-naphthyl)ethylamine (+), (–), aminomethylpinone, N,N-dimethyl-1-phenylethylamine, N-methyl-1-phenylethylamine, 4-nitrophenylethylamine, pseudoephedrine, norephedrine, norpseudoephedrine, amino acid derivatives, peptide derivatives.

The compounds of the general formula I according to the invention can be prepared, for example, by reacting the carboxylic acid derivatives of the general formula VI in which the substituents have the stated meaning with compounds of the general formula VII

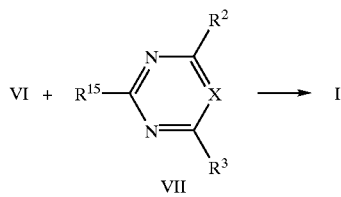

where R$^{15}$ is halogen or R$^{16}$—SO$_2$—, where R$^{16}$ can be C$_1$–C$_4$-alkyl, C$_1$–C$_4$-haloalkyl or phenyl. The reaction preferably takes place in one of the abovementioned inert diluents with the addition of a suitable base, ie. a base which deprotonates the intermediate VI, at a temperature in the range from room temperature to the boiling point of the solvent.

Compounds of the formula VII are known, and some of them can be bought, or they can be prepared in a conventional manner.

It is possible to use as base an alkali metal or alkaline earth metal hydride such as sodium hydride, potassium hydride or calcium hydride, a carbonate such as an alkali metal carbonate, eg. sodium or potassium carbonate, an alkali metal or alkaline earth metal hydroxide such as sodium or potassium hydroxide, an organometallic compound such as butyllithium or an alkali metal amide such as lithium diisopropylamide or lithium amide.

Compounds of the formula I can also be prepared by starting from the corresponding carboxylic acids, ie. compounds of the formula I where R$^1$ is hydroxyl, and initially converting these in a conventional way into an activated form, such as a halide, an anhydride or imidazolide, and then reacting the latter with an appropriate hydroxyl compound HOR$^{10}$. This reaction can be carried out in conventional solvents and often requires the addition of a base, in which case those mentioned above are suitable. These two steps can also be simplified, for example, by allowing the carboxylic acid to act on the hydroxyl compound in the presence of a dehydrating agent such as a carbodiimide.

Compounds of the formula I can also be prepared by starting from the salts of the appropriate carboxylic acids, ie.

from compounds of the formula I where R is a group $COR^1$ and $R^1$ is OM, where M can be an alkali metal cation or the equivalent of an alkaline earth metal cation. These salts can be reacted with many compounds of the formula $R^1$-A where A is a conventional nucleofugic leaving group, for example halogen such as chlorine, bromine, iodine or aryl- or alkyl-sulfonyl which is unsubstituted or substituted by halogen, alkyl or haloalkyl, such as toluenesulfonyl and methylsulfonyl, or another equivalent leaving group. Compounds of the formula $R^1$-A with a reactive substituent A are known or can easily be obtained with general expert knowledge. This reaction can be carried out in conventional solvents and is advantageously carried out with the addition of a base, in which case those mentioned above are suitable.

The radical R in formula I can be varied widely. R is, for example, a group

where $R^1$ has the following meanings:

a) hydrogen;

b) a succinylimidoxy [sic] group;

c) a 5-membered heteroaromatic system linked via a nitrogen atom, such as pyrrolyl, pyrazolyl, imidazolyl and triazolyl, which may carry one or two halogen atoms, in particular fluorine and chlorine, and/or one or two of the following radicals:

$C_1$–$C_4$-alkyl such as methyl, ethyl, 1-propyl, 2-propyl, 2-methyl-2-propyl, 2-methyl-1-propyl, 1-butyl, 2-butyl;

$C_1$–$C_4$-haloalkyl, in particular $C_1$–$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$–$C_4$-haloalkoxy, in particular $C_1$–$C_2$-haloalkoxy such as difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy;

$C_1$–$C_4$-alkoxy such as methoxy, ethoxy, propoxy, 1-methylethoxy, butoxy, 1-methylpropoxy, 2-methylpropoxy, 1,1-dimethylethoxy, in particular methoxy, ethoxy and 1-methylethoxy;

$C_1$–$C_4$-alkylthio such as methylthio, ethylthio, propylthio, 1-methylethylthio, butylthio, 1-methylpropylthio, 2-methylpropylthio, 1,1-dimethylethylthio, in particular methylthio and ethylthio;

d) $R^1$ is furthermore a radical

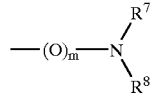

where m is 0 or 1 and $R^7$ and $R^8$, which can be identical or different, have the following meanings:

hydrogen, $C_1$–$C_8$-alkyl, in particular $C_1$–$C_4$-alkyl as mentioned above;

$C_3$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl--3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethy-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, in particular 2-propynyl;

$C_3$–$C_8$-cycloalkyl, such as cyclopropyl, cyclobutyl, cyclopentyl, cyclohexyl and [sic] cycloheptyl, cyclooctyl, it being possible for these alkyl, cycloalkyl, alkenyl and alkynyl groups each to carry one to five halogen atoms, in particular fluorine or chlorine, and/or one or two of the following groups:

$C_1$–$C_4$-alkyl, $C_1$–$C_4$-alkoxy, $C_1$–$C_4$-alkylthio, $C_1$–$C_4$-haloalkoxy as mentioned above, $C_3$–$C_6$-alkenyloxy, $C_3$–$C_6$-alkenylthio, $C_3$–$C_6$-alkynyloxy, $C_3$–$C_6$-alkynylthio, where the alkenyl and alkynyl constituents present in these radicals preferably correspond to the abovementioned meanings;

$C_1$–$C_4$-alkylcarbonyl such as, in particular, methylcarbonyl, ethylcarbonyl, propylcarbonyl, 1-methylethylcarbonyl, butylcarbonyl, 1-methylpropylcarbonyl, 2-methylpropylcarbonyl and 1,1-dimethylethylcarbonyl;

$C_1$–$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl and 1,1-dimethylethoxycarbonyl;

$C_3$–$C_6$-alkenylcarbonyl, $C_3$–$C_6$-alkynylcarbonyl, $C_3$–$C_6$-alkenyloxy-carbonyl and $C_3$–$C_6$-alkynyloxycarbonyl, where the alkenyl and alkynyl radicals preferably have the definitions detailed above;

phenyl, unsubstituted or substituted one or more times, eg. one to three times by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkyl-thio, such as 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl and 2,6-difluorophenyl;

di-$C_1$–$C_4$-alkylamino such as, in particular, dimethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^7$ and $R^8$ furthermore phenyl which can be substituted by one or more, eg. one to three, of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio as mentioned above in particular;

or $R^7$ and $R^8$ together form a $C_4$–$C_7$-alkylene chain which is closed to form a ring and is unsubstituted or substituted, eg. substituted by $C_1$–$C_4$-alkyl, and which may contain a hetero atom selected from the group of oxygen, sulfur or nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_2)_3$—; —NH—$(CH_2)_3$—, —$CH_2$—NH—$(CH_2)$—$CH_2$—CH=CH—$CH_2$—, —CH=CH—$(CH_2)_3$—;

e) $R^1$ is furthermore a group

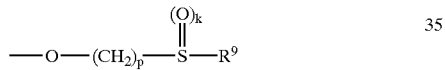

in which k assumes the values 0, 1 and 2, p assumes the values 1, 2, 3 and 4, and $R^9$ is
$C_1$–$C_4$-alkyl, $C_1$–$C_4$-haloalkyl, $C_3$–$C_6$-alkenyl, $C_3$–$C_6$-alkynyl or unsubstituted or substituted phenyl, as mentioned above in particular;

f) $R^1$ is furthermore a radical $OR^{10}$ where $R^{10}$ is:
hydrogen, the cation of an alkali metal such as lithium, sodium, potassium or the cation of an alkaline earth metal such as calcium, magnesium and barium, or an environmentally compatible organic ammonium ion such as tertiary $C_1$–$C_4$-alkylammonium or the ammonium ion;

$C_3$–$C_8$-cycloalkyl as mentioned above, which may carry one to three $C_1$–$C_4$-alkyl groups;

$C_1$–$C_8$-alkyl such as, in particular, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which may carry one to five halogen atoms, in particular fluorine and chlorine, and/or one of the following radicals:

$C_1$–$C_4$-alkoxy, $C_1$–$C_4$-alkylthio, cyano, $C_1$–$C_4$-alkylcarbonyl, $C_3$–$C_8$-cycloakyl [sic], $C_1$–$C_4$-alkoxycarbonyl, phenyl, phenoxy or phenylcarbonyl, it being possible for the aromatic radicals in turn each to carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio as mentioned above in particular;

a $C_1$–$C_8$-alkyl group as mentioned above, which can carry one to five halogen atoms, in particular fluorine and/or chlorine, and carries one of the following radicals: a 5-membered heteroaromatic system containing one to three nitrogen atoms, or a 5-membered heteroaromatic system containing one nitrogen atom and one oxygen or sulfur atom, which system may carry one to four halogen atoms and/or one or two of the following radicals:

nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropyl-5-isoxazolyl, 3-methyl-5-isoxazolyl, 2-oxazolyl, 2-thiazolyl, 2-imidazolyl, 3-ethyl-5-isoxazolyl, 3-phenyl-5-isoxazolyl, 3-tert-butyl-5-isoxazolyl;

a $C_2$–$C_6$-alkyl group which carries in position 2 one of the following radicals: $C_1$–$C_4$-alkoxyimino, $C_3$–$C_6$-alkynyloxyimino, $C_3$–$C_6$-haloalkenyloxyimino or benzyloxyimino;

a $C_3$–$C_6$-alkenyl or $C_3$–$C_6$-alkynyl group, it being possible for these groups in turn to carry one to five halogen atoms;

$R^{10}$ is furthermore a phenyl radical which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio as mentioned above in particular;

a 5-membered heteroaromatic system which is linked via a nitrogen atom and contains one to three nitrogen atoms and which can carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloro-1-imidazolyl;

$R^{10}$ is furthermore a group

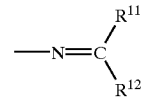

where $R^{11}$ and $R^{12}$, which can be identical or different, are:

$C_1$–$C_8$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or an unsubstituted or substituted phenyl radical; phenyl which may be substituted by one or more, for example one to three, of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, where these radicals correspond to those mentioned above in particular;

or $R^{11}$ and $R^{12}$ together form a $C_3$–$C_{12}$-alkylene chain which may carry one to three $C_1$–$C_4$-alkyl groups and may contain a hetero atom from the group of oxygen, sulfur and nitrogen;

g) $R^1$ is furthermore a radical

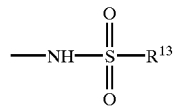

where $R^{13}$ is:

$C_1$–$C_4$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or phenyl radical;

phenyl, unsubstituted or substituted;

h) $R^1$ is a radical

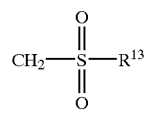

where $R^{13}$ has the abovementioned meaning.

R can furthermore be: tetrazole [sic] or nitrile [sic].

With a view to the biological effect, preferred carboxylic acid derivatives of the general formula I, both as pure enantiomers and pure diastereomers or as a mixture thereof, are those in which the substituents have the following meanings:

$R^2$ the $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio groups and halogen atoms specified for $R^1$, in particular chlorine, methyl, methoxy, ethoxy, di-fluoromethoxy and trifluoromethoxy;

X nitrogen or $CR^{14}$ where $R^{14}$ hydrogen or alkyl, or $CR^{14}$ forms together with $CR^3$ a 4- or 5-membered alkylene or alkenylene ring in which, in each case, a methylene group can be replaced by oxygen or sulfur, such as —$CH_2$–$CH_2$—O—, —CH=CH—O—, —$CH_2$—$CH_2$—$CH_2$—O—, —CH=CH—$CH_2$—O—, in particular hydrogen, —$CH_2$—$CH_2$—O—, —CH($CH_3$)—CH($CH_3$)—O—, —C($CH_3$)=C($CH_3$)—O—, —CH=C($CH_3$)—O— or —C($CH_3$)=C($CH_3$)—S;

$R^3$ the $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio groups and halogen atoms mentioned for $R^1$, in particular chlorine, methyl, methoxy, ethoxy, difluoromethoxy, trifluoromethoxy or is linked to $R^{14}$ as mentioned above to form a 5- or 6-membered ring;

$R^4$ and $R^5$ are phenyl or naphthyl, each of which can be substituted by one or more, eg. one to three, of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl, $C_1$–$C_4$-alkoxycarbonyl;

phenyl or naphthyl which are connected together in ortho positions by a direct linkage, a methylene, ethylene or ethenylene group, an oxygen or sulfur atom or an $SO_2$, NH or N-alkyl group, or $C_3$–$C_7$-cycloalkyl;

$R^6$ $C_1$–$C_4$-alkyl, $C_3$–$C_5$-alkenyl, where the radicals are each substituted once or twice by hydroxyl, mercapto, carboxyl or cyano;

Z sulfur or oxygen.

Particularly preferred compounds of the formula I, both as pure enantiomers and pure diastereomers or as a mixture thereof, are those in which the substituents have the following meanings:

$R^2$ $C_1$–$C_4$-alkyl, $C_1$–$C_4$-alkoxy,

X nitrogen or $CR^{14}$ where $R^{14}$ is hydrogen or alkyl, or $CR^{14}$ forms together with $CR^3$ a 4- or 5-membered alkylene or alkenylene ring, such as —$CH_2$—$CH_2$—$CH_2$— or —CH=CH—$CH_2$—, in which, in each case, a methylene group can be replaced by oxygen or sulfur, such as —$CH_2$—$CH_2$—O—, —CH=CH—O—, —$CH_2$—$CH_2$—$CH_2$—O—, —CH=CH—$CH_2$—O—, in particular hydrogen, —$CH_2$—$CH_2$—O—, —CH($CH_3$)—CH($CH_3$)—O—, —C($CH_3$)=C($CH_3$)—O—, —CH=C($CH_3$)—O—or —C($CH_3$)=C($CH_3$)—S;

$R^3$ the $C_1$–$C_4$-alkyl-, $C_1$–$C_4$-alkoxy, $C_1$–$C_4$-alkylthio groups mentioned for $R^1$, or is linked to $R^{14}$ as mentioned above to form a 5- or 6-membered ring;

$R^4$ and $R^5$ phenyl (identical or different), which can be substituted by one or more, eg. one to three, of the following radicals: halogen, nitro, hydroxyl, $C_1$–$C_4$-alkyl, $C_1$–$C_4$-alkoxy, $C_1$–$C_4$-alkylthio or $R^4$ and $R^5$ are phenyl groups which are connected together in ortho positions by a direct linkage, a methylene, ethylene or ethenylene group, an oxygen or sulfur atom or an $SO_2$, NH or N-alkyl group; or $R^4$ and $R^5$ are $C_3$–$C_7$-cycloalkyl;

$R^6$ $C_1$–$C_3$-alkyl, $C_3$–$C_4$-alkenyl, where the radicals are each substituted once or twice by hydroxyl or are substituted once by carboxyl;

Z sulfur or oxygen.

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, or hypertension or kidney failure caused by ischemia or intoxication, and cancers, especially prostate and skin cancer.

The invention further relates to the combination of compounds of the formula I with inhibitors of the renin-angiotensin system (RAS). RAS inhibitors are disclosed in, for example, EP 634 175.

The combinations according to the invention are suitable for treating disorders for which compounds of the formula I also show efficacy on their own, especially for treating hypertomy [sic] and chronic heart failure.

The good effect of the compounds can be shown in the following tests:

Receptor Binding Studies

Cloned human $ET_A$ receptor-expressing CHO cells and guinea pig cerebellar membranes with >60% $ET_B$ compared with ETA receptors were used for the binding studies.

Membrane Preparation

The $ET_A$ receptor-expressing CHO cells were grown in $F_{12}$ medium containing 10% fetal calf serum, 1% glutamine, 100 U/ml penicillin and 0.2% streptomycin (Gibco BRL, Gaithersburg, Md., USA). After 48 h, the cells were washed with PBS and incubated with 0.05% trypsin-containing PBS for 5 min. Neutralization was then carried out with $F_{12}$ medium, and the cells were collected by centrifugation at 300×g. To lyze the cells, the pellet was briefly washed with lysis buffer (5 mM tris-HCl, pH 7.4 with 10% glycerol) and then incubated at a concentration of $10^7$ cells/ml of lysis buffer at 4° C. for 30 min. The membranes were centrifuged at 20,000×g for 10 min, and the pellet was stored in liquid nitrogen.

Guinea pig cerebella were homogenized in a Potter-Elvejhem homogenizer and obtained by differential centrifugation at 1000×g for 10 min and repeated centrifugation of the supernatant at 20,000×g for 10 min.

Binding Assays

For the $ET_A$ and $ET_B$ receptor binding assay, the membranes were suspended in an incubation bufer (50 mM tris-HCl, pH 7.4 with 5 mM $MnCl_2$, 40 µg/ml bacitracin and 0.2% BSA) at a concentration of 50 µg of protein per assay mixture and incubated with 25 pM [125I [sic]]-$ET_1$ ($ET_A$ receptor assay) or 25 pM [125I [sic]]-$RZ_3$ ($ET_B$ receptor assay) in the presence and absence of test substance at 25° C. The nonspecific binding was determined using $10^{-7}$M $ET_1$. After 30 min, filtration through GF/B glass fiber filters (Whatman, England) in a Skatron cell collector (Skatron, Lier, Norway) was carried out to separate free and bound radioligand, and the filters were washed with ice-cold tris-HCl buffer, pH 7.4 with 0.2% BSA. The radioactivity collected on the filters was quantified using a Packard 2200 CA liquid scintillation counter.

Functional in Vitro Assay System to Look for Endothelin Receptor (subtype A) Antagonists This assay system is a functional, cell-based assay for endothelin receptors. When certain cells are stimulated with endothelin 1 (ET1) they show an increase in the intracellular calcium concentration. This increase can be measured in intact cells loaded with calcium-sensitive dyes.

1-Fibroblasts which have been isolated from rats and in which an endogenous endothelin receptor of the A subtype had been detected were loaded with the fluorescent dye Fura 2-an as follows: after trypsinization, the cells were resuspended in buffer A (120 mM NaCl, 5 mM KCl, 1.5 mM $MgCl_2$, 1 mM $CaCl_2$, 25 mM HEPES, 10 mM glucose, pH 7.4) to a density of $2\times10^6$/ml and incubated with Fura 2-am (2 µM), Pluronics [sic] F-127 (0.04%) and DMSO (0.2%) at 37° C. in the dark for 30 min. The cells were then washed twice with buffer A and resuspended at $2\times10^6$/ml.

The fluorescence signal from $2\times10^5$ cells per ml with Ex/Em 380/510 was recorded continuously at 30° C. The test substances and, after an incubation time of 3 min, ET1 were [lacuna] to the cells, the maximum change in the fluorescence was determined. The response of the cells to ET1 without previous addition of a test substance was used as control and was set equal to 100%.

Testing of ET Antagonists in Vivo

Male SD rats weighing 250–300 g were anesthetized with amorbarbital, artificially ventilated, vagotomized and pithed. The carotid artery and jugular vein were cathetized.

In control animals, intravenous administration of 1 µg/kg ET1 leads to a distinct rise in blood pressure which persists for a lengthy period.

The test animals received an i.v. injection of the test compounds (1 ml/kg) 5 min before the administration of ET1. To determine the ET-antagonistic properties, the rise in blood pressure in the test animals was compared with that in the control animals.

Endothelin-1-induced Sudden Death in Mice

The principle of the test is the inhibition of the sudden heart death caused in mice by endothelin, which is probably induced by constriction of the coronary vessels, by pretreatment with endothelin receptor antagonists. Intravenous injection of 10 nmol/kg of endothelin in a volume of 5 ml/kg of body weight results in death of the animals within a few minutes.

The lethal endothelin-1 dose is checked in each case on a small group of animals. If the test substance is administered intravenously, the endothelin-1 injection which was lethal in the reference group usually takes place 5 min thereafter. With other modes of administration, the times before administration are extended, where appropriate up to several hours.

The survival rate is recorded, and effective doses which protect 50% of the animals (ED 50) from endothelin-induced heart death for 24 h or longer are determined.

Functional Test on Vessels for Endothelin Receptor Antagonists

Segments of rabbit aorta are, after an initial tension of 2 g and a relaxation time of 1 h in Krebs-Henseleit solution at 37° C. and pH 7.3–7.4, first induced to contract with $K^+$. After washing out, an endothelin dose-effect plot up to the maximum is constructed.

Potential endothelin antagonists are administered to other preparations of the same vessel 15 min before starting the endothelin dose-effect plot. The effects of the endothelin are calculated as percent of the $K^+$induced contraction. Effective endothelin antagonists result in a shift to the right in the endothelin dose-effect plot.

The compounds according to the invention can be administered orally or parenterally (subcutaneously, intravenously, intramuscularly, intraperotoneally) in a conventional way. Administration can also take place with vapours or sprays through the nasopharyngeal space.

The dosage depends on the age, condition and weight of the patient and on the mode of administration. The daily dose of active substance is, as a rule, about 0.5–50 mg/kg of body weight on oral administration and about 0.1–10 mg/kg of body weight on parenteral administration.

The novel compounds can be used in conventional solid or liquid pharmaceutical administration forms, eg. as uncoated or (film) coated tablets, capsules, powders, granules, suppositories, solutions, ointments, creams or sprays. These are produced in a conventional way. The active substances can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of the active substance.

SYNTHESIS EXAMPLE

Example 1

Methyl 3-(2-Acetoxyethoxy)-2-hydroxy-3,3-diphenylpropionate 7.95 g (31.3 mmol) of methyl 3,3-diphenyl-2,3-epoxypropionate were dissolved in 20 ml of diethyl ether under $N_2$ and cooled to 0° C., and 5.87 ml (31.3 mmol) of 2-hydroxyethyl acetate (50% strength) and 3 drops of $BF_3.Et_2O$ were added. After removal of the ice bath, the mixture was stirred at RT for 2 h.

The reaction solution was washed successively with NaCl solution and $NaHCO_3$ solution, and the organic phase was dried over $MgSO_4$ and concentrated. 12.3 g of a pale yellow oil were obtained and were reacted without further purification and characterization.

Example 2

Methyl 3-(2-Acetoxyethoxy)-2-(4-methoxy-6-methyl-2-pyrimidinyloxy)-3,3-diphenylpropionate 4 g (11.1 mmol) of methyl 3-(2-acetoxyethoxy)-2-hydroxy-3,3-di-phenylpropionate were dissolved in 20 ml of DMF under $N_2$, 770 mg (5.6 mmol) of $K_2CO_3$ and 2.24 g (11.1 mmol) of 2-methanesulfonyl-4-methoxy-6-methylpyrimidine were added, and the mixture was stirred at 80° C. for 2 h. It was subsequently diluted with 20 ml of $H_2O$ and extracted twice with 30 ml of diethyl ether, the organic phase was dried over $MgSO_4$ and concentrated, and the residue was purified by chromatography on silica gel with ethyl acetate/cyclohexane mixtures. 4.8 g (90%) of a colorless oil were obtained.

$^1$H-NMR ($CDCl_3$) δ: 2.10 (s, 3H); 2.35 (s, 3H); 3.50 (s, 3H); 3.85 (s, 6H); 4.00 (m, 2H); 4.30 (m, 2H); 6.00 (s, 1H), 6.25 (s, 1H) 7.20–7.50 (m, 10H).

Example 3

3-(2-Hydroxyethoxy)-2-(4-methoxy-6-methyl-2-pyrimidinyloxy)-3,3-diphenylpropionic Acid 10 4.8 g (10 mmol) of methyl 3-(2-acetoxyethoxy)-2-(4-methoxy-6-methyl-2-pyrimidinyloxy(3,3-diphenylpropionate [sic] were dissolved in 80 ml of dioxane and 40ml of 1N KOH solution and stirred at 90° C. for 8 h. The solution was diluted with 50 ml of $H_2O$ and extracted with diethyl ether. The aqueous phase was neutralized with 10 ml of 1N HCl solution and extracted twice with diethyl ether, and the organic phase was dried and concentrated. The residue was purified by chromatography on silica gel with cyclohexane/ethyl acetate mixtures, and crystallization from diethyl ether/hexane resulted in 1.2 g (28%) of colorless crystals.

$^1$H-NMR ($CDCl_3$) δ: 2.25 (s, 3H); 3.55 (m, 2H); 3.65–3.85 (m, 3H); 3.90 (s, 6H), 6.10 (s, 1H); 6.25 (s, 1H); 6.40 (broad, 1H), 7.20–7.60 (m, 10H).

Example 4

Methyl 3-(2-Hydroxy-2-methoxycarbonyl-1,1-diphenylethoxy)-2,2-dimethylpropionate 12.7 g (50 mmol) of methyl 3,3-diphenyl-2,3-epoxypropionate were dissolved in 50 ml of diethyl ether, 6.6 g (50 mmol) of methyl 3-hydroxy-2,2-dimethylpropionate and 1 ml of $BF_3.Et_2O$ were added, and the mixture was stirred at room temperature for 18 h. The solvent was evaporated off, and the oily residue was reacted without further purification and characterization.

Example 5

Methyl 3-[2-Methoxycarbonyl-2-(4-methoxy-6-methyl-2-pyrimidinyloxy)-1,1-diphenylethoxy]-2,2-dimethylpropionate 10 g (25.9 mmol) of methyl 3-(2-hydroxy-2-methoxycarbonyl-1,1-di-phenylethoxy)-2,2-dimethylpropionate were dissolved in 40 ml of DMF under $N_2$, 1.78 g (13 mmol) of $K_2CO_3$ and 5.2 g (25.9 mmol) of 2-methanesulfonyl-4-methoxy-6-methylpyrimidine were added, and the mixture was stirred at 80° C. for 2 h. It was subsequently diluted with 40 ml of $H_2O$ and extracted twice with 30 ml of diethyl ether, the organic phase was dried over $MgSO_4$ and concentrated, and the residue was purified by chromatography on silica gel with ethyl acetate/cyclohexane mixtures. Crystallization from diethyl ether/hexane resulted in 11.8 g (90%) of the product as colorless crystals.

Melting point: 143° C.

Example 6

3-[2–Carboxy-2-(4-methoxy-6-methyl-2-pyrimidinyloxy)-1,1-diphenylethoxy]-2,2-dimethylpropionic Acid 10.1 g (20 mmol) of methyl 3-[2-methoxycarbonyl-2-(4-methoxy-6-methyl-2-pyrimidinyloxy)-1,1-diphenylethoxy]-2,2-di-methylpropionate were dissolved in 50 ml of dioxane and 50 ml of 2N NaOH solution and stirred at 80° C. for 4 h. The solution was diluted with 300 ml of $H_2O$ and extracted with 100 ml of ethyl acetate. The aqueous phase was neutralized with 1N HCl and extracted with ethyl acetate, and the organic phase was dried over $MgSO_4$, filtered and concentrated. The oily residue was crystallized from diethyl ether/hexane to result in 4.1 g (42%) of colorless crystals.

$^1$H-NMR ($CDCl_3$) δ: 1.10 (s, 3H); 1.20 (s, 3H); 2.50 (s, 3H); 3.65 (d, 1H); 3.80 (s, 3H); 3.90 (d, 1H); 5.95 (s, 1H); 6.25 (s, 1H); 7.20–7.50 (m, 10H)

The compounds listed in Table 1 can be prepared in similar ways.

TABLE 1

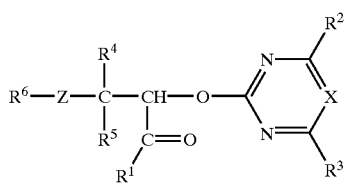

| No. | $R^1$ | $R^4$, $R^5$ | $R^6$ | $R^2$ | $R^3$ | X | Z |
|---|---|---|---|---|---|---|---|
| 1. | OH | Phenyl | $H_2NC(O)$—$CH_2$— | OMe | $CH_2$—$CH_2$—$CH_2$—C | O |
| 2. | OH | Phenyl | HO—$CH_2$—$CH_2$— | OMe | Me | CH | O |
| 3. | OH | Phenyl | HO—$CH_2$—$CH_2$— | Me | Me | CH | O |
| 4. | OH | Phenyl | HO—$CH_2$—$CH_2$— | Me | Et | CH | O |
| 5. | OH | Phenyl | HO—$CH_2$—$CH_2$— | OMe | $CH_2$—$CH_2$—$CH_2$—C | O |
| 6. | OH | Phenyl | HO—$CH_2$—$CH_2$— | OMe | O—$CH_2$—$CH_2$—C | O |
| 7. | OH | Phenyl | HO—$CH_2$—$CH_2$— | Me | $CH_2$—$CH_2$—$CH_2$—C | O |

TABLE 1-continued

| No. | R¹ | R⁴, R⁵ | R⁶ | R² | R³ | X | Z |
|---|---|---|---|---|---|---|---|
| 8. | OH | Phenyl | HO—CH$_2$—CH$_2$— | OMe | OMe | N | O |
| 9. | OH | Phenyl | HO—CH$_2$—CH$_2$— | NMe$_2$ | NMe$_2$ | N | O |
| 10. | OH | Phenyl | HO—CH$_2$—CH$_2$— | Et | Et | CH | O |
| 11. | OH | Phenyl | HO—CH$_2$—CH(OH)—CH$_2$— | OMe | OMe | CH | O |
| 12. | OH | Phenyl | HO—CH$_2$—CH(OH)—CH$_2$— | OMe | Me | CH | O |
| 13. | OH | Phenyl | HO—CH$_2$—CH(OH)—CH$_2$— | Me | Me | CH | O |
| 14. | OH | Phenyl | HO—CH$_2$—CH(OH)—CH$_2$— | Me | Et | CH | O |
| 15. | OH | Phenyl | HO—CH$_2$—CH(OH)—CH$_2$— | OMe | CH$_2$—CH$_2$—CH$_2$—C | O |
| 16. | OH | Phenyl | HO—CH$_2$—CH(OH)—CH$_2$— | OMe | O—CH$_2$—CH$_2$—C | O |
| 17. | OH | Phenyl | HO—CH$_2$—CH(OH)—CH$_2$— | Me | CH$_2$—CH$_2$—CH$_2$—C | O |
| 18. | OH | Phenyl | HO—CH$_2$—CH(OH)—CH$_2$— | OMe | OMe | N | O |
| 19. | OH | Phenyl | HO—CH$_2$—CH(OH)—CH$_2$— | NMe$_2$ | NMe$_2$ | N | O |
| 20. | OH | Phenyl | HO—CH$_2$—CH(OH)—CH$_2$— | Et | Et | CH | O |
| 21. | OH | o-F-phenyl | HO—CH$_2$—CH$_2$— | OMe | OMe | CH | O |
| 22. | OH | o-F-phenyl | HO—CH$_2$—CH$_2$— | Me | Me | CH | O |
| 23. | OH | m-F-phenyl | HO—CH$_2$—CH$_2$— | Me | Et | CH | O |
| 24. | OH | m-OMe-phenyl | HO—CH$_2$—CH$_2$— | OMe | CH$_2$—CH$_2$—CH$_2$—C | O |
| 25. | OH | m-Me-phenyl | HO—CH$_2$—CH$_2$— | OMe | O—CH$_2$—CH$_2$—C | O |
| 26. | OH | p-Cl-phenyl | HO—CH$_2$—CH$_2$— | Me | CH$_2$—CH$_2$—CH$_2$—C | O |
| 27. | OH | p-F-phenyl | HO—CH$_2$—CH$_2$— | OMe | OMe | N | O |
| 28. | OH | m-OMe-phenyl | HO—CH$_2$—CH$_2$— | NMe$_2$ | NMe$_2$ | N | O |
| 29. | OH | m-OMe-phenyl | HO—CH$_2$—CH$_2$— | Et | Et | CH | O |
| 30. | OH | o-F-phenyl | HO—CH$_2$—CH(OH)—CH$_2$— | OMe | OMe | CH | O |
| 31. | OH | m-F-phenyl | HO—CH$_2$—CH(OH)—CH$_2$— | OMe | Me | CH | O |
| 32. | OH | m-Me-phenyl | HO—CH$_2$—CH(OH)—CH$_2$— | Me | Me | CH | O |
| 33. | OH | m-OMe-phenyl | HO—CH$_2$—CH(OH)—CH$_2$— | Me | Et | CH | O |
| 34. | OH | p-Me-phenyl | HO—CH$_2$—CH(OH)—CH$_2$— | OMe | CH$_2$—CH$_2$—CH$_2$—C | O |
| 35. | OH | p-Cl-phenyl | HO—CH$_2$—CH(OH)—CH$_2$— | OMe | O—CH$_2$—CH$_2$—C | O |
| 36. | OH | p-F-phenyl | HO—CH$_2$—CH(OH)—CH$_2$— | Me | CH$_2$—CH$_2$—CH$_2$—C | O |
| 37. | OH | m-Me-phenyl | HO—CH$_2$—CH(OH)—CH$_2$— | OMe | OMe | N | O |
| 38. | OH | p-Cl-phenyl | HO—CH$_2$—CH(OH)—CH$_2$— | NMe$_2$ | NMe$_2$ | N | O |
| 39. | OH | p-Cl-phenyl | HO—CH$_2$—CH(OH)—CH$_2$— | Et | Et | CH | O |
| 40. | OH | Phenyl | (HO—CH$_2$)$_2$CH—CH$_2$— | OMe | OMe | CH | O |
| 41. | OH | Phenyl | (HO—CH$_2$)$_2$CH—CH$_2$— | OMe | Me | CH | O |
| 42. | OH | Phenyl | (HO—CH$_2$)$_2$CH—CH$_2$— | Me | Me | CH | O |
| 43. | OH | Phenyl | (HO—CH$_2$)$_2$CH—CH$_2$— | Me | Et | CH | O |
| 44. | OH | Phenyl | (HO—CH$_2$)$_2$CH—CH$_2$— | OMe | CH$_2$—CH$_2$—CH$_2$—C | O |
| 45. | OH | Phenyl | (HO—CH$_2$)$_2$CH—CH$_2$— | OMe | O—CH$_2$—CH$_2$—C | O |
| 46. | OH | Phenyl | (HO—CH$_2$)$_2$CH—CH$_2$— | Me | CH$_2$—CH$_2$—CH$_2$—C | O |
| 47. | OH | Phenyl | (HO—CH$_2$)$_2$CH—CH$_2$— | OMe | OMe | N | O |
| 48. | OH | Phenyl | (HO—CH$_2$)$_2$CH—CH$_2$— | NMe$_2$ | NMe$_2$ | N | O |
| 49. | OH | Phenyl | (HO—CH$_2$)$_2$CH—CH$_2$— | Et | Et | CH | O |
| 50. | OH | Phenyl | CH$_3$—CH$_2$—(HO—CH$_2$)$_2$—CH$_2$— | OMe | OMe | CH | O |
| 51. | OH | Phenyl | CH$_3$—CH$_2$—(HO—CH$_2$)$_2$—CH$_2$— | OMe | Me | CH | O |
| 52. | OH | Phenyl | CH$_3$—CH$_2$—(HO—CH$_2$)$_2$—CH$_2$— | Me | Me | CH | O |
| 53. | OH | Phenyl | CH$_3$—CH$_2$—(HO—CH$_2$)$_2$—CH$_2$— | Me | Et | CH | O |
| 54. | OH | Phenyl | CH$_3$—CH$_2$—(HO—CH$_2$)$_2$—CH$_2$— | OMe | CH$_2$—CH$_2$—CH$_2$—C | O |
| 55. | OH | Phenyl | CH$_3$—CH$_2$—(HO—CH$_2$)$_2$—CH$_2$— | OMe | O—CH$_2$—CH$_2$—C | O |
| 56. | OH | Phenyl | CH$_3$—CH$_2$—(HO—CH$_2$)$_2$—CH$_2$— | Me | CH$_2$—CH$_2$—CH$_2$—C | O |
| 57. | OH | Phenyl | CH$_3$—CH$_2$—(HO—CH$_2$)$_2$—CH$_2$— | OMe | OMe | N | O |
| 58. | OH | Phenyl | CH$_3$—CH$_2$—(HO—CH$_2$)$_2$—CH$_2$— | NMe$_2$ | NMe$_2$ | N | O |
| 59. | OH | Phenyl | CH$_3$—CH$_2$—(HO—CH$_2$)$_2$—CH$_2$— | Et | Et | CH | O |
| 60. | OH | o-F-phenyl | (HO—CH$_2$)$_2$CH—CH$_2$— | OMe | OMe | CH | O |
| 61. | OH | m-F-phenyl | (HO—CH$_2$)$_2$CH—CH$_2$— | OMe | Me | CH | O |
| 62. | OH | p-F-phenyl | (HO—CH$_2$)$_2$CH—CH$_2$— | Me | Me | CH | O |
| 63. | OH | m-OMe-phenyl | (HO—CH$_2$)$_2$CH—CH$_2$— | Me | Et | CH | O |
| 64. | OH | m-Me-phenyl | (HO—CH$_2$)$_2$CH—CH$_2$— | OMe | CH$_2$—CH$_2$—CH$_2$—C | O |
| 65. | OH | p-Cl-phenyl | (HO—CH$_2$)$_2$CH—CH$_2$— | OMe | O—CH$_2$—CH$_2$—C | O |
| 66. | OH | p-Me-phenyl | (HO—CH$_2$)$_2$CH—CH$_2$— | Me | CH$_2$—CH$_2$—CH$_2$—C | O |
| 67. | OH | m-F-phenyl | (HO—CH$_2$)$_2$CH—CH$_2$— | OMe | OMe | N | O |
| 68. | OH | m-OMe-phenyl | (HO—CH$_2$)$_2$CH—CH$_2$— | NMe$_2$ | NMe$_2$ | N | O |
| 69. | OH | m-OMe-phenyl | (HO—CH$_2$)$_2$CH—CH$_2$— | Et | Et | CH | O |
| 70. | OH | p-Me-phenyl | CH$_3$—CH$_2$—(HO—CH$_2$)$_2$—CH$_2$— | OMe | OMe | CH | O |
| 71. | OH | p-Cl-phenyl | CH$_3$—CH$_2$—(HO—CH$_2$)$_2$—CH$_2$— | OMe | Me | CH | O |
| 72. | OH | m-OMe-phenyl | CH$_3$—CH$_2$—(HO—CH$_2$)$_2$—CH$_2$— | Me | Me | CH | O |
| 73. | OH | m-Me-phenyl | CH$_3$—CH$_2$—(HO—CH$_2$)$_2$—CH$_2$— | Me | Et | CH | O |
| 74. | OH | m-F-phenyl | CH$_3$—CH$_2$—(HO—CH$_2$)$_2$—CH$_2$— | OMe | CH$_2$—CH$_2$—CH$_2$—C | O |

TABLE 1-continued

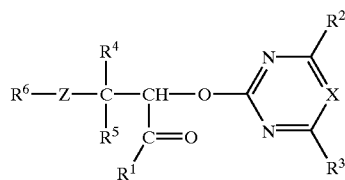

| No. | R¹ | R⁴, R⁵ | R⁶ | R² | R³ | X | Z |
|---|---|---|---|---|---|---|---|
| 75. | OH | p-F-phenyl | CH₃—CH₂—(HO—CH₂)₂—CH₂— | OMe | O—CH₂—CH₂—C | O | |
| 76. | OH | o-F-phenyl | CH₃—CH₂—(HO—CH₂)₂—CH₂— | Me | CH₂—CH₂—CH₂—C | O | |
| 77. | OH | p-Cl-phenyl | CH₃—CH₂—(HO—CH₂)₂—CH₂— | OMe | OMe | N | O |
| 78. | OH | m-F-phenyl | CH₃—CH₂—(HO—CH₂)₂—CH₂— | NMe₂ | NMe₂ | N | O |
| 79. | OH | m-F-phenyl | CH₃—CH₂—(HO—CH₂)₂—CH₂— | Et | Et | CH | O |
| 80. | OH | Phenyl | HO—(CH₂)₃— | OMe | OMe | CH | O |
| 81. | OH | Phenyl | HO—(CH₂)₃— | OMe | Me | CH | O |
| 82. | OH | Phenyl | HO—(CH₂)₃— | Me | Me | CH | O |
| 83. | OH | Phenyl | HO—(CH₂)₃— | Me | Et | CH | O |
| 84. | OH | Phenyl | HO—(CH₂)₃— | OMe | CH₂—CH₂—CH₂—C | O | |
| 85. | OH | Phenyl | HO—(CH₂)₃— | OMe | O—CH₂—CH₂—C | O | |
| 86. | OH | Phenyl | HO—(CH₂)₃— | Me | CH₂—CH₂—CH₂—C | O | |
| 87. | OH | Phenyl | HO—(CH₂)₃— | OMe | OMe | N | O |
| 88. | OH | Phenyl | HO—(CH₂)₃— | NMe₂ | NMe₂ | N | O |
| 89. | OH | Phenyl | HO—(CH₂)₃— | Et | Et | CH | O |
| 90. | OH | Phenyl | HO—(CH₂)₄— | OMe | OMe | CH | O |
| 91. | OH | Phenyl | HO—(CH₂)₄— | OMe | Me | CH | O |
| 92. | OH | Phenyl | HO—(CH₂)₄— | Me | Me | CH | O |
| 93. | OH | Phenyl | HO—(CH₂)₄— | Me | Et | CH | O |
| 94. | OH | Phenyl | HO—(CH₂)₄— | OMe | CH₂—CH₂—CH₂—C | O | |
| 95. | OH | Phenyl | HO—(CH₂)₄— | OMe | O—CH₂—CH₂—C | O | |
| 96. | OH | Phenyl | HO—(CH₂)₄— | Me | CH₂—CH₂—CH₂—C | O | |
| 97. | OH | Phenyl | HO—(CH₂)₄— | OMe | OMe | N | O |
| 98. | OH | Phenyl | HO—(CH₂)₄— | NMe₂ | NMe₂ | N | O |
| 99. | OH | Phenyl | HO—(CH₂)₄— | Et | Et | CH | O |
| 100. | OH | o-F-phenyl | HO—(CH₂)₃— | OMe | Me | CH | O |
| 101. | OH | o-F-phenyl | HO—(CH₂)₃— | Me | Me | CH | O |
| 102. | OH | m-F-phenyl | HO—(CH₂)₃— | Me | Et | CH | O |
| 103. | OH | m-OMe-phenyl | HO—(CH₂)₃— | OMe | CH₂—CH₂—CH₂—C | O | |
| 104. | OH | m-Me-phenyl | HO—(CH₂)₃— | OMe | O—CH₂—CH₂—C | O | |
| 105. | OH | p-Cl-phenyl | HO—(CH₂)₃— | Me | CH₂—CH₂—CH₂—C | O | |
| 106. | OH | p-F-phenyl | HO—(CH₂)₃— | OMe | OMe | N | O |
| 107. | OH | m-OMe-phenyl | HO—(CH₂)₃— | NMe₂ | NMe₂ | N | O |
| 108. | OH | m-OMe-phenyl | HO—(CH₂)₃— | Et | Et | CH | O |
| 109. | OH | o-F-phenyl | HO—(CH₂)₄— | OMe | OMe | CH | O |
| 110. | OH | m-F-phenyl | HO—(CH₂)₄— | OMe | Me | CH | O |
| 111. | OH | m-Me-phenyl | HO—(CH₂)₄— | Me | Me | CH | O |
| 112. | OH | m-OMe-phenyl | HO—(CH₂)₄— | Me | Et | CH | O |
| 113. | OH | p-Me-phenyl | HO—(CH₂)₄— | OMe | CH₂—CH₂—CH₂—C | O | |
| 114. | OH | p-Cl-phenyl | HO—(CH₂)₄— | OMe | O—CH₂—CH₂—C | O | |
| 115. | OH | p-F-phenyl | HO—(CH₂)₄— | Me | CH₂—CH₂—CH₂—C | O | |
| 116. | OH | m-Me-phenyl | HO—(CH₂)₄— | OMe | OMe | N | O |
| 117. | OH | p-Cl-phenyl | HO—(CH₂)₄— | NMe₂ | NMe₂ | N | O |
| 118. | OH | p-Cl-phenyl | HO—(CH₂)₄— | Et | Et | CH | O |
| 119. | OH | Phenyl | HO₂C—CH₂— | OMe | OMe | CH | O |
| 120. | OH | Phenyl | HO₂C—CH₂— | OMe | OEt | CH | O |
| 121. | OH | Phenyl | HO₂C—CH₂— | OMe | Me | CH | O |
| 122. | OH | Phenyl | HO₂C—CH₂— | Me | Me | CH | O |
| 123. | OH | Phenyl | HO₂C—CH₂— | Me | Et | CH | O |
| 124. | OH | Phenyl | HO₂C—CH₂— | OMe | CH₂—CH₂—CH₂—C | O | |
| 125. | OH | Phenyl | HO₂C—CH₂— | OMe | O—CH₂—CH₂—C | O | |
| 126. | OH | Phenyl | HO₂C—CH₂— | Me | CH₂—CH₂—CH₂—C | O | |
| 127. | OH | Phenyl | HO₂C—CH₂— | OMe | OMe | N | O |
| 128. | OH | Phenyl | HO₂C—CH₂— | NMe₂ | NMe₂ | N | O |
| 129. | OH | Phenyl | HO₂C—CH₂— | Et | Et | CH | O |
| 130. | OH | Phenyl | HO₂C—(CH₂)₂— | OMe | OMe | CH | O |
| 131. | OH | Phenyl | HO₂C—(CH₂)₂— | OMe | Me | CH | O |
| 132. | OH | Phenyl | HO₂C—(CH₂)₂— | Me | Me | CH | O |
| 133. | OH | Phenyl | HO₂C—(CH₂)₂— | Me | Et | CH | O |
| 134. | OH | Phenyl | HO₂C—(CH₂)₂— | OMe | CH₂—CH₂—CH₂—C | O | |
| 135. | OH | Phenyl | HO₂C—(CH₂)₂— | OMe | O—CH₂—CH₂—C | O | |
| 136. | OH | Phenyl | HO₂C—(CH₂)₂— | Me | CH₂—CH₂—CH₂—C | O | |
| 137. | OH | Phenyl | HO₂C—(CH₂)₂— | OMe | OMe | N | O |
| 138. | OH | Phenyl | HO₂C—(CH₂)₂— | NMe₂ | NMe₂ | N | O |
| 139. | OH | Phenyl | HO₂C—(CH₂)₂— | Et | Et | CH | O |
| 140. | OH | o-F-phenyl | HO₂C—CH₂— | OMe | OMe | CH | O |
| 141. | OH | o-F-phenyl | HO₂C—CH₂— | Me | Me | CH | O |

TABLE 1-continued

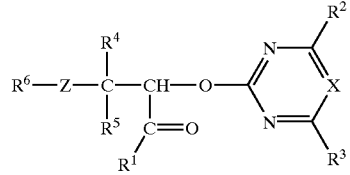

| No. | R¹ | R⁴, R⁵ | R⁶ | R² | R³ | X | Z |
|---|---|---|---|---|---|---|---|
| 142. | OH | m-F-phenyl | HO₂C—CH₂— | Me | Et | CH | O |
| 143. | OH | m-OMe-phenyl | HO₂C—CH₂— | OMe | CH₂—CH₂—CH₂—C | O |
| 144. | OH | m-Me-phenyl | HO₂C—CH₂— | OMe | O—CH₂—CH₂—C | O |
| 145. | OH | p-Cl-phenyl | HO₂C—CH₂— | Me | CH₂—CH₂—CH₂—C | O |
| 146. | OH | p-F-phenyl | HO₂C—CH₂— | OMe | OMe | N | O |
| 147. | OH | m-OMe-phenyl | HO₂C—CH₂— | NMe₂ | NMe₂ | N | O |
| 148. | OH | o-F-phenyl | HO₂C—(CH₂)₂— | OMe | OMe | CH | O |
| 149. | OH | m-F-phenyl | HO₂C—(CH₂)₂— | OMe | Me | CH | O |
| 150. | OH | m-Me-phenyl | HO₂C—(CH₂)₂— | Me | Me | CH | O |
| 151. | OH | m-OMe-phenyl | HO₂C—(CH₂)₂— | Me | Et | CH | O |
| 152. | OH | p-Me-phenyl | HO₂C—(CH₂)₂— | OMe | CH₂—CH₂—CH₂—C | O |
| 153. | OH | p-Cl-phenyl | HO₂C—(CH₂)₂— | OMe | O—CH₂—CH₂—C | O |
| 154. | OH | p-F-phenyl | HO₂C—(CH₂)₂— | Me | CH₂—CH₂—CH₂—C | O |
| 155. | OH | m-OMe-phenyl | HO₂C—(CH₂)₂— | OMe | OMe | N | O |
| 156. | OH | p-Cl-phenyl | HO₂C—(CH₂)₂— | NMe₂ | NMe₂ | N | O |
| 157. | OH | p-Cl-phenyl | HO₂C—(CH₂)₂— | Et | Et | CH | O |
| 158. | OH | Phenyl | HO₂C—(CH₂)₃— | OMe | OMe | CH | O |
| 159. | OH | Phenyl | HO₂C—(CH₂)₃— | OMe | Me | CH | O |
| 160. | OH | Phenyl | HO₂C—(CH₂)₃— | Me | Me | CH | O |
| 161. | OH | Phenyl | HO₂C—(CH₂)₃— | Me | Et | CH | O |
| 162. | OH | Phenyl | HO₂C—(CH₂)₃— | OMe | CH₂—CH₂—CH₂—C | O |
| 163. | OH | Phenyl | HO₂C—(CH₂)₃— | OMe | O—CH₂—CH₂—C | O |
| 164. | OH | Phenyl | HO₂C—(CH₂)₃— | Me | CH₂—CH₂—CH₂—C | O |
| 165. | OH | Phenyl | HO₂C—(CH₂)₃— | OMe | OMe | N | O |
| 166. | OH | Phenyl | HO₂C—(CH₂)₃— | NMe₂ | NMe₂ | N | O |
| 167. | OH | Phenyl | HO₂C—(CH₂)₃— | Et | Et | CH | O |
| 168. | OH | Phenyl | HO₂C—CH(CH₃)—CH₂— | OMe | OMe | CH | O |
| 169. | OH | Phenyl | HO₂C—CH(CH₃)—CH₂— | OMe | Me | CH | O |
| 170. | OH | Phenyl | HO₂C—CH(CH₃)—CH₂— | Me | Me | CH | O |
| 171. | OH | Phenyl | HO₂C—CH(CH₃)—CH₂— | Me | Et | CH | O |
| 172. | OH | Phenyl | HO₂C—CH(CH₃)—CH₂— | OMe | CH₂—CH₂—CH₂—C | O |
| 173. | OH | Phenyl | HO₂C—CH(CH₃)—CH₂— | OMe | O—CH₂—CH₂—C | O |
| 174. | OH | Phenyl | HO₂C—CH(CH₃)—CH₂— | Me | CH₂—CH₂—CH₂—C | O |
| 175. | OH | Phenyl | HO₂C—CH(CH₃)—CH₂— | OMe | OMe | N | O |
| 176. | OH | Phenyl | HO₂C—CH(CH₃)—CH₂— | NMe₂ | NMe₂ | N | O |
| 177. | OH | Phenyl | HO₂C—CH(CH₃)—CH₂— | Et | Et | CH | O |
| 178. | OH | o-F-phenyl | HO₂C—(CH₂)₃— | OMe | Me | CH | O |
| 179. | OH | o-F-phenyl | HO₂C—(CH₂)₃— | Me | Me | CH | O |
| 180. | OH | m-F-phenyl | HO₂C—(CH₂)₃— | Me | Et | CH | O |
| 181. | OH | m-OMe-phenyl | HO₂C—(CH₂)₃— | OMe | CH₂—CH₂—CH₂—C | O |
| 182. | OH | m-OMe-phenyl | HO₂C—(CH₂)₃— | OMe | O—CH₂—CH₂—C | O |
| 183. | OH | p-Cl-phenyl | HO₂C—(CH₂)₃— | Me | CH₂—CH₂—CH₂—C | O |
| 184. | OH | p-F-phenyl | HO₂C—(CH₂)₃— | OMe | OMe | N | O |
| 185. | OH | m-OMe-phenyl | HO₂C—(CH₂)₃— | NMe₂ | NMe₂ | N | O |
| 186. | OH | m-OMe-phenyl | HO₂C—(CH₂)₃— | Et | Et | CH | O |
| 187. | OH | o-F-phenyl | HO₂C—CH(CH₃)—CH₂ | OMe | OMe | CH | O |
| 188. | OH | m-F-phenyl | HO₂C—CH(CH₃)—CH₂ | OMe | Me | CH | O |
| 189. | OH | m-Me-phenyl | HO₂C—CH(CH₃)—CH₂ | Me | Me | CH | O |
| 190. | OH | m-OMe-phenyl | HO₂C—CH(CH₃)—CH₂ | Me | Et | CH | O |
| 191. | OH | p-Me-phenyl | HO₂C—CH(CH₃)—CH₂ | OMe | CH₂—CH₂—CH₂—C | O |
| 192. | OH | p-Cl-phenyl | HO₂C—CH(CH₃)—CH₂ | OMe | O—CH₂—CH₂—C | O |
| 193. | OH | p-F-phenyl | HO₂C—CH(CH₃)—CH₂ | Me | CH₂—CH₂—CH₂—C | O |
| 194. | OH | m-Me-phenyl | HO₂C—CH(CH₃)—CH₂ | OMe | OMe | N | O |
| 195. | OH | p-Cl-phenyl | HO₂C—CH(CH₃)—CH₂ | NMe₂ | NMe₂ | N | O |
| 196. | OH | p-Cl-phenyl | HO₂C—CH(CH₃)—CH₂ | Et | Et | CH | O |
| 197. | OH | Phenyl | HO₂C—C(CH₃)₂—CH₂— | OMe | OMe | CH | O |
| 198. | OH | Phenyl | HO₂C—C(CH₃)₂—CH₂— | OMe | Me | CH | O |
| 199. | OH | Phenyl | HO₂C—C(CH₃)₂—CH₂— | Me | Me | CH | O |
| 200. | OH | Phenyl | HO₂C—C(CH₃)₂—CH₂— | Me | Et | CH | O |
| 201. | OH | Phenyl | HO₂C—C(CH₃)₂—CH₂— | OMe | CH₂—CH₂—CH₂—C | O |
| 202. | OH | Phenyl | HO₂C—C(CH₃)₂—CH₂— | OMe | O—CH₂—CH₂—C | O |
| 203. | OH | Phenyl | HO₂C—C(CH₃)₂—CH₂— | Me | CH₂—CH₂—CH₂—C | O |
| 204. | OH | Phenyl | HO₂C—C(CH₃)₂—CH₂— | OMe | OMe | N | O |
| 205. | OH | Phenyl | HO₂C—C(CH₃)₂—CH₂— | NMe₂ | NMe₂ | N | O |
| 206. | OH | Phenyl | HO₂C—C(CH₃)₂—CH₂— | Et | Et | CH | O |
| 207. | OH | Phenyl | H₂NC(O)—CH₂— | OMe | OMe | CH | O |
| 208. | OH | Phenyl | H₂NC(O)—CH₂— | OMe | Me | CH | O |

TABLE 1-continued

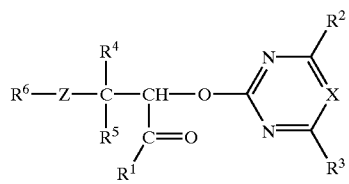

| No. | R¹ | R⁴, R⁵ | R⁶ | R² | R³ | X | Z |
|---|---|---|---|---|---|---|---|
| 209. | OH | Phenyl | H₂NC(O)—CH₂— | Me | Me | CH | O |
| 210. | OH | Phenyl | H₂NC(O)—CH₂— | Me | Et | CH | O |
| 211. | OH | Phenyl | H₂NC(O)—CH₂— | OMe | CH₂—CH₂—CH₂—C | O |
| 212. | OH | Phenyl | H₂NC(O)—CH₂— | OMe | O—CH₂—CH₂—C | O |
| 213. | OH | Phenyl | H₂NC(O)—CH₂— | Me | CH₂—CH₂—CH₂—C | O |
| 214. | OH | Phenyl | H₂NC(O)—CH₂— | OMe | OMe | N | O |
| 215. | OH | Phenyl | H₂NC(O)—CH₂— | NMe₂ | NMe₂ | N | O |
| 216. | OH | Phenyl | H₂NC(O)—CH₂— | Et | Et | CH | O |
| 217. | OH | o-F-phenyl | HO₂C—C(CH₃)₂—CH₂— | OMe | Me | CH | O |
| 218. | OH | o-F-phenyl | HO₂C—C(CH₃)₂—CH₂— | Me | Me | CH | O |
| 219. | OH | m-F-phenyl | HO₂C—C(CH₃)₂—CH₂— | Me | Et | CH | O |
| 220. | OH | m-OMe-phenyl | HO₂C—C(CH₃)₂—CH₂— | OMe | CH₂—CH₂—CH₂—C | O |
| 221. | OH | m-Me-phenyl | HO₂C—C(CH₃)₂—CH₂— | Me | O—CH₂—CH₂—C | O |
| 222. | OH | p-Cl-phenyl | HO₂C—C(CH₃)₂—CH₂— | Me | CH₂—CH₂—CH₂—C | O |
| 223. | OH | p-F-phenyl | HO₂C—C(CH₃)₂—CH₂— | OMe | OMe | N | O |
| 224. | OH | m-OMe-phenyl | HO₂C—C(CH₃)₂—CH₂— | NMe₂ | NMe₂ | N | O |
| 225. | OH | m-OMe-phenyl | HO₂C—C(CH₃)₂—CH₂— | Et | Et | CH | O |
| 226. | OH | o-F-phenyl | H₂NC(O)—CH₂— | OMe | OMe | CH | O |
| 227. | OH | m-F-phenyl | H₂NC(O)—CH₂— | OMe | Me | CH | O |
| 228. | OH | m-Me-phenyl | H₂NC(O)—CH₂— | Me | Me | CH | O |
| 229. | OH | m-OMe-phenyl | H₂NC(O)—CH₂— | Me | Et | CH | O |
| 230. | OH | p-Me-phenyl | H₂NC(O)—CH₂— | Me | CH₂—CH₂—CH₂—C | O |
| 231. | OH | p-Cl-phenyl | H₂NC(O)—CH₂— | OMe | O—CH₂—CH₂—C | O |
| 232. | OH | p-F-phenyl | H₂NC(O)—CH₂— | Me | CH₂—CH₂—CH₂—C | O |
| 233. | OH | m-Me-phenyl | H₂NC(O)—CH₂— | OMe | OMe | N | O |
| 234. | OH | p-Cl-phenyl | H₂NC(O)—CH₂— | NMe₂ | NMe₂ | N | O |
| 235. | OH | p-Cl-phenyl | H₂NC(O)—CH₂— | Et | Et | CH | O |
| 236. | OH | Phenyl | H₂NC(O)—(CH₂)₂— | OMe | OMe | CH | O |
| 237. | OH | Phenyl | H₂NC(O)—(CH₂)₂— | OMe | Me | CH | O |
| 238. | OH | Phenyl | H₂NC(O)—(CH₂)₂— | Me | Me | CH | O |
| 239. | OH | Phenyl | H₂NC(O)—(CH₂)₂— | Me | Et | CH | O |
| 240. | OH | Phenyl | H₂NC(O)—(CH₂)₂— | Me | CH₂—CH₂—CH₂—C | O |
| 241. | OH | Phenyl | H₂NC(O)—(CH₂)₂— | OMe | O—CH₂—CH₂—C | O |
| 242. | OH | Phenyl | H₂NC(O)—(CH₂)₂— | Me | CH₂—CH₂—CH₂—C | O |
| 243. | OH | Phenyl | H₂NC(O)—(CH₂)₂— | OMe | OMe | N | O |
| 244. | OH | Phenyl | H₂NC(O)—(CH₂)₂— | NMe₂ | NMe₂ | N | O |
| 245. | OH | Phenyl | H₂NC(O)—(CH₂)₂— | Et | Et | CH | O |
| 246. | OH | Phenyl | H₂NC(NH)—CH₂— | OMe | OMe | CH | O |
| 247. | OH | Phenyl | H₂NC(NH)—CH₂— | OMe | Me | CH | O |
| 248. | OH | Phenyl | H₂NC(NH)—CH₂— | Me | Me | CH | O |
| 249. | OH | Phenyl | H₂NC(NH)—CH₂— | Me | Et | CH | O |
| 250. | OH | Phenyl | H₂NC(NH)—CH₂— | OMe | CH₂—CH₂—CH₂—C | O |
| 251. | OH | Phenyl | H₂NC(NH)—CH₂— | OMe | O—CH₂—CH₂—C | O |
| 252. | OH | Phenyl | H₂NC(NH)—CH₂— | Me | CH₂—CH₂—CH₂—C | O |
| 253. | OH | Phenyl | H₂NC(NH)—CH₂— | OMe | OMe | N | O |
| 254. | OH | Phenyl | H₂NC(NH)—CH₂— | NMe₂ | NMe₂ | N | O |
| 255. | OH | Phenyl | H₂NC(NH)—CH₂— | Et | Et | CH | O |
| 256. | OH | o-F-phenyl | H₂NC(O)—(CH₂)₂— | OMe | Me | CH | O |
| 257. | OH | o-F-phenyl | H₂NC(O)—(CH₂)₂— | Me | Me | CH | O |
| 258. | OH | m-F-phenyl | H₂NC(O)—(CH₂)₂— | Me | Et | CH | O |
| 259. | OH | m-OMe-phenyl | H₂NC(O)—(CH₂)₂— | OMe | CH₂—CH₂—CH₂C | O |
| 260. | OH | m-OMe-phenyl | H₂NC(O)—(CH₂)₂— | OMe | O—CH₂—CH₂C | O |
| 261. | OH | p-Cl-phenyl | H₂NC(O)—(CH₂)₂— | Me | CH₂—CH₂—CH₂C | O |
| 262. | OH | p-F-phenyl | H₂NC(O)—(CH₂)₂— | OMe | OMe | N | O |
| 263. | OH | m-OMe-phenyl | H₂NC(O)—(CH₂)₂— | NMe₂ | NMe₂ | N | O |
| 264. | OH | m-OMe-phenyl | H₂NC(O)—(CH₂)₂— | Et | Et | CH | O |
| 265. | OH | o-F-phenyl | H₂NC(NH)—CH₂— | OMe | OMe | CH | O |
| 266. | OH | m-F-phenyl | H₂NC(NH)—CH₂— | OMe | Me | CH | O |
| 267. | OH | m-Me-phenyl | H₂NC(NH)—CH₂— | Me | Me | CH | O |
| 268. | OH | m-OMe-phenyl | H₂NC(NH)—CH₂— | Me | Et | CH | O |
| 269. | OH | p-Me-phenyl | H₂NC(NH)—CH₂— | OMe | CH₂—CH₂—CH₂—C | O |
| 270. | OH | p-Cl-phenyl | H₂NC(NH)—CH₂— | OMe | O—CH₂—CH₂—C | O |
| 271. | OH | p-F-phenyl | H₂NC(NH)—CH₂— | Me | CH₂—CH₂—CH₂—C | O |
| 272. | OH | m-Me-phenyl | H₂NC(NH)—CH₂— | OMe | OMe | N | O |
| 273. | OH | p-Cl-phenyl | H₂NC(NH)—CH₂— | NMe₂ | NMe₂ | N | O |
| 274. | OH | p-Cl-phenyl | H₂NC(NH)—CH₂— | Et | Et | CH | O |
| 275. | OH | Phenyl | H₂NC(NH)—(CH₂)₂— | OMe | OMe | CH | O |

TABLE 1-continued

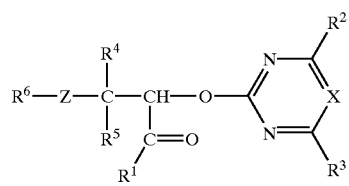

| No. | R¹ | R⁴, R⁵ | R⁶ | R² | R³ | X | Z |
|---|---|---|---|---|---|---|---|
| 276. | OH | Phenyl | H₂NC(NH)—(CH₂)₂— | OMe | Me | CH | O |
| 277. | OH | Phenyl | H₂NC(NH)—(CH₂)₂— | Me | Me | CH | O |
| 278. | OH | Phenyl | H₂NC(NH)—(CH₂)₂— | Me | Et | CH | O |
| 279. | OH | Phenyl | H₂NC(NH)—(CH₂)₂— | OMe | CH₂—CH₂—CH₂—C | O |
| 280. | OH | Phenyl | H₂NC(NH)—(CH₂)₂— | OMe | O—CH₂—CH₂—C | O |
| 281. | OH | Phenyl | H₂NC(NH)—(CH₂)₂— | Me | CH₂—CH₂—CH₂—C | O |
| 282. | OH | Phenyl | H₂NC(NH)—(CH₂)₂— | OMe | OMe | N | O |
| 283. | OH | Phenyl | H₂NC(NH)—(CH₂)₂— | NMe₂ | NMe₂ | N | O |
| 284. | OH | Phenyl | H₂NC(NH)—(CH₂)₂— | Et | Et | CH | O |
| 285. | OH | Phenyl | NC—CH₂— | OMe | OMe | CH | O |
| 286. | OH | Phenyl | NC—CH₂— | OMe | Me | CH | O |
| 287. | OH | Phenyl | NC—CH₂— | Me | Me | CH | O |
| 288. | OH | Phenyl | NC—CH₂— | Me | Et | CH | O |
| 289. | OH | Phenyl | NC—CH₂— | OMe | CH₂—CH₂—CH₂—C | O |
| 290. | OH | Phenyl | NC—CH₂— | OMe | O—CH₂—CH₂—C | O |
| 291. | OH | Phenyl | NC—CH₂— | Me | CH₂—CH₂—CH₂—C | O |
| 292. | OH | Phenyl | NC—CH₂— | OMe | OMe | N | O |
| 293. | OH | Phenyl | NC—CH₂— | NMe₂ | NMe₂ | N | O |
| 294. | OH | Phenyl | NC—CH₂— | Et | Et | CH | O |
| 295. | OH | o-F-phenyl | H₂NC(NH)—(CH₂)₂— | OMe | Me | CH | O |
| 296. | OH | o-F-phenyl | H₂NC(NH)—(CH₂)₂— | Me | Me | CH | O |
| 297. | OH | m-F-phenyl | H₂NC(NH)—(CH₂)₂— | Me | Et | CH | O |
| 298. | OH | m-OMe-phenyl | H₂NC(NH)—(CH₂)₂— | OMe | CH₂—CH₂—CH₂C | O |
| 299. | OH | m-Me-phenyl | H₂NC(NH)—(CH₂)₂— | OMe | O—CH₂—CH₂C | O |
| 300. | OH | p-Cl-phenyl | H₂NC(NH)—(CH₂)₂— | Me | CH₂—CH₂—CH₂C | O |
| 301. | OH | p-F-phenyl | H₂NC(NH)—(CH₂)₂— | OMe | OMe | N | O |
| 302. | OH | m-OMe-phenyl | H₂NC(NH)—(CH₂)₂— | NMe₂ | NMe₂ | N | O |
| 303. | OH | m-OMe-phenyl | H₂NC(NH)—(CH₂)₂— | Et | Et | CH | O |
| 304. | OH | o-F-phenyl | NC—CH₂— | OMe | OMe | CH | O |
| 305. | OH | m-F-phenyl | NC—CH₂— | OMe | Me | CH | O |
| 306. | OH | m-Me-phenyl | NC—CH₂— | Me | Me | CH | O |
| 307. | OH | m-OMe-phenyl | NC—CH₂— | Me | Et | CH | O |
| 308. | OH | p-Me-phenyl | NC—CH₂— | OMe | CH₂—CH₂—CH₂—C | O |
| 309. | OH | p-Cl-phenyl | NC—CH₂— | OMe | O—CH₂—CH₂—C | O |
| 310. | OH | p-F-phenyl | NC—CH₂— | Me | CH₂—CH₂—CH₂—C | O |
| 311. | OH | m-Me-phenyl | NC—CH₂— | OMe | OMe | N | O |
| 312. | OH | p-Cl-phenyl | NC—CH₂— | NMe₂ | NMe₂ | N | O |
| 313. | OH | p-Cl-phenyl | NC—CH₂— | Et | Et | CH | O |
| 314. | OH | Phenyl | NC(CH₂)₂— | OMe | OMe | CH | O |
| 315. | OH | Phenyl | NC(CH₂)₂— | Me | Me | CH | O |
| 316. | OH | Phenyl | NC(CH₂)₂— | Me | Et | CH | O |
| 317. | OH | Phenyl | NC(CH₂)₂— | OMe | CH₂—CH₂—CH₂C | O |
| 318. | OH | Phenyl | NC(CH₂)₂— | OMe | O—CH₂—CH₂C | O |
| 319. | OH | Phenyl | NC(CH₂)₂— | Me | CH₂—CH₂—CH₂C | O |
| 320. | OH | Phenyl | NC(CH₂)₂— | OMe | OMe | N | O |
| 321. | OH | Phenyl | NC(CH₂)₂— | NMe₂ | NMe₂ | N | O |
| 322. | OH | Phenyl | NC(CH₂)₂— | Et | Et | CH | O |
| 323. | OH | Phenyl | NC(CH₂)₃— | OMe | OMe | CH | O |
| 324. | OH | Phenyl | NC(CH₂)₃— | OMe | Me | CH | O |
| 325. | OH | Phenyl | NC(CH₂)₃— | Me | Me | CH | O |
| 326. | OH | Phenyl | NC(CH₂)₃— | Me | Et | CH | O |
| 327. | OH | Phenyl | NC(CH₂)₃— | OMe | CH₂—CH₂—CH₂—C | O |
| 328. | OH | Phenyl | NC(CH₂)₃— | OMe | O—CH₂—CH₂—C | O |
| 329. | OH | Phenyl | NC(CH₂)₃— | Me | CH₂—CH₂—CH₂—C | O |
| 330. | OH | Phenyl | NC(CH₂)₃— | OMe | OMe | N | O |
| 331. | OH | Phenyl | NC(CH₂)₃— | NMe₂ | NMe₂ | N | O |
| 332. | OH | Phenyl | NC(CH₂)₃— | Et | Et | CH | O |
| 333. | OH | o-F-phenyl | NC—(CH₂)₂— | OMe | Me | CH | O |
| 334. | OH | o-F-phenyl | NC—(CH₂)₂— | Me | Me | CH | O |
| 335. | OH | m-F-phenyl | NC—(CH₂)₂— | Me | Et | CH | O |
| 336. | OH | m-OMe-phenyl | NC—(CH₂)₂— | OMe | CH₂—CH₂—CH₂C | O |
| 337. | OH | m-OMe-phenyl | NC—(CH₂)₂— | OMe | O—CH₂—CH₂C | O |
| 338. | OH | p-Cl-phenyl | NC—(CH₂)₂— | Me | CH₂—CH₂—CH₂C | O |
| 339. | OH | p-F-phenyl | NC—(CH₂)₂— | OMe | OMe | N | O |
| 340. | OH | m-OMe-phenyl | NC—(CH₂)₂— | NMe₂ | NMe₂ | N | O |
| 341. | OH | m-OMe-phenyl | NC—(CH₂)₂— | Et | Et | CH | O |
| 342. | OH | o-F-phenyl | NC—(CH₂)₃— | OMe | OMe | CH | O |

TABLE 1-continued

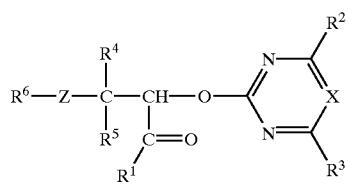

| No. | R¹ | R⁴, R⁵ | R⁶ | R² | R³ | X | Z |
|---|---|---|---|---|---|---|---|
| 343. | OH | m-F-phenyl | NC—(CH₂)₃— | OMe | Me | CH | O |
| 344. | OH | m-Me-phenyl | NC—(CH₂)₃— | Me | Me | CH | O |
| 345. | OH | m-OMe-phenyl | NC—(CH₂)₃— | Me | Et | CH | O |
| 346. | OH | p-Me-phenyl | NC—(CH₂)₃— | OMe | CH₂—CH₂—CH₂—C | O |
| 347. | OH | p-Cl-phenyl | NC—(CH₂)₃— | OMe | O—CH₂—CH₂—C | O |
| 348. | OH | p-F-phenyl | NC—(CH₂)₃— | Me | CH₂—CH₂—CH₂—C | O |
| 349. | OH | m-Me-phenyl | NC—(CH₂)₃— | OMe | OMe | N | O |
| 350. | OH | p-Cl-phenyl | NC—(CH₂)₃— | NMe₂ | NMe₂ | N | O |
| 351. | OH | p-Cl-phenyl | NC—(CH₂)₃— | Et | Et | CH | O |
| 352. | OH | Phenyl | CH₃—SO₂—CH₂— | OMe | Me | CH | O |
| 353. | OH | Phenyl | CH₃—SO₂—CH₂— | Me | Me | CH | O |
| 354. | OH | Phenyl | CH₃—SO₂—CH₂— | Me | Et | CH | O |
| 355. | OH | Phenyl | CH₃—SO₂—CH₂— | OMe | CH₂—CH₂—CH₂C | O |
| 356. | OH | Phenyl | CH₃—SO₂—CH₂— | OMe | O—CH₂—CH₂C | O |
| 357. | OH | Phenyl | CH₃—SO₂—CH₂— | Me | CH₂—CH₂—CH₂C | O |
| 358. | OH | Phenyl | CH₃—SO₂—CH₂— | OMe | OMe | N | O |
| 359. | OH | Phenyl | CH₃—SO₂—CH₂— | NMe₂ | NMe₂ | N | O |
| 360. | OH | Phenyl | CH₃—SO₂—CH₂— | Et | Et | CH | O |
| 361. | OH | Phenyl | H₃C—SO₂—CH₂—CH₂— | OMe | OMe | CH | O |
| 362. | OH | Phenyl | H₃C—SO₂—CH₂—CH₂— | OMe | Me | CH | O |
| 363. | OH | Phenyl | H₃C—SO₂—CH₂—CH₂— | Me | Me | CH | O |
| 364. | OH | Phenyl | H₃C—SO₂—CH₂—CH₂— | Me | Et | CH | O |
| 365. | OH | Phenyl | H₃C—SO₂—CH₂—CH₂— | OMe | CH₂—CH₂—CH₂—C | O |
| 366. | OH | Phenyl | H₃C—SO₂—CH₂—CH₂— | OMe | O—CH₂—CH₂—C | O |
| 367. | OH | Phenyl | H₃C—SO₂—CH₂—CH₂— | Me | CH₂—CH₂—CH₂—C | O |
| 368. | OH | Phenyl | H₃C—SO₂—CH₂—CH₂— | OMe | OMe | N | O |
| 369. | OH | Phenyl | H₃C—SO₂—CH₂—CH₂— | NMe₂ | NMe₂ | N | O |
| 370. | OH | Phenyl | H₃C—SO₂—CH₂—CH₂— | Et | Et | CH | O |
| 371. | OH | o-F-phenyl | H₃C—SO₂—CH₂— | OMe | Me | CH | O |
| 372. | OH | o-F-phenyl | H₃C—SO₂—CH₂— | Me | Me | CH | O |
| 373. | OH | m-F-phenyl | H₃C—SO₂—CH₂— | Me | Et | CH | O |
| 374. | OH | m-OMe-phenyl | H₃C—SO₂—CH₂— | OMe | CH₂—CH₂—CH₂C | O |
| 375. | OH | m-OMe-phenyl | H₃C—SO₂—CH₂— | OMe | O—CH₂—CH₂C | O |
| 376. | OH | p-Cl-phenyl | H₃C—SO₂—CH₂— | Me | CH₂—CH₂—CH₂C | O |
| 377. | OH | p-F-phenyl | H₃C—SO₂—CH₂— | OMe | OMe | N | O |
| 378. | OH | m-OMe-phenyl | H₃C—SO₂—CH₂— | NMe₂ | NMe₂ | N | O |
| 379. | OH | m-OMe-phenyl | H₃C—SO₂—CH₂— | Et | Et | CH | O |
| 380. | OH | o-F-phenyl | H₃C—SO₂—CH₂—CH₂— | OMe | OMe | CH | O |
| 381. | OH | m-F-phenyl | H₃C—SO₂—CH₂—CH₂— | OMe | Me | CH | O |
| 382. | OH | m-Me-phenyl | H₃C—SO₂—CH₂—CH₂— | Me | Me | CH | O |
| 383. | OH | m-OMe-phenyl | H₃C—SO₂—CH₂—CH₂— | Me | Et | CH | O |
| 384. | OH | p-Me-phenyl | H₃C—SO₂—CH₂—CH₂— | OMe | CH₂—CH₂—CH₂—C | O |
| 385. | OH | p-Cl-phenyl | H₃C—SO₂—CH₂—CH₂— | OMe | O—CH₂—CH₂—C | O |
| 386. | OH | p-F-phenyl | H₃C—SO₂—CH₂—CH₂— | Me | CH₂—CH₂—CH₂—C | O |
| 387. | OH | m-Me-phenyl | H₃C—SO₂—CH₂—CH₂— | OMe | OMe | N | O |
| 388. | OH | p-Cl-phenyl | H₃C—SO₂—CH₂—CH₂— | NMe₂ | NMe₂ | N | O |
| 389. | OH | p-Cl-phenyl | H₃C—SO₂—CH₂—CH₂— | Et | Et | CH | O |
| 390. | OH | Phenyl | HS—CH₂—CH₂— | OMe | Me | CH | O |
| 391. | OH | Phenyl | HS—CH₂—CH₂— | Me | Me | CH | O |
| 392. | OH | Phenyl | HS—CH₂—CH₂— | Me | Et | CH | O |
| 393. | OH | Phenyl | HS—CH₂—CH₂— | OMe | CH₂—CH₂—CH₂C | O |
| 394. | OH | Phenyl | HS—CH₂—CH₂— | OMe | O—CH₂—CH₂C | O |
| 395. | OH | Phenyl | HS—CH₂—CH₂— | Me | CH₂—CH₂—CH₂C | O |
| 396. | OH | Phenyl | HS—CH₂—CH₂— | OMe | OMe | N | O |
| 397. | OH | Phenyl | HS—CH₂—CH₂— | NMe₂ | NMe₂ | N | O |
| 398. | OH | Phenyl | HS—CH₂—CH₂— | Et | Et | CH | O |
| 399. | OH | o-F-phenyl | H₃C—SO₂—CH₂— | OMe | Me | CH | O |
| 400. | OH | o-F-phenyl | HS—CH₂—CH₂— | Me | Me | CH | O |
| 401. | OH | m-F-phenyl | HS—CH₂—CH₂— | Me | Et | CH | O |
| 402. | OH | m-OMe-phenyl | HS—CH₂—CH₂— | OMe | CH₂—CH₂—CH₂C | O |
| 403. | OH | m-OMe-phenyl | HS—CH₂—CH₂— | OMe | O—CH₂—CH₂C | O |
| 404. | OH | p-Cl-phenyl | HS—CH₂—CH₂— | Me | CH₂—CH₂—CH₂C | O |
| 405. | OH | p-F-phenyl | HS—CH₂—CH₂— | OMe | OMe | N | O |
| 406. | OH | m-OMe-phenyl | HS—CH₂—CH₂— | NMe₂ | NMe₂ | N | O |
| 407. | OH | m-OMe-phenyl | HS—CH₂—CH₂— | Et | Et | CH | O |

We claim:

1. A compound of formula I

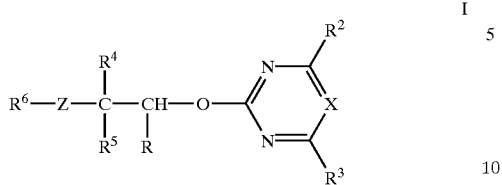

where R is a group —(CO)—$R^1$
where $R^1$ is:
a) a radical

where m is 0 or 1 and $R^7$ and $R^8$, which can be identical or different, have the following meanings: hydrogen, $C_1$–$C_8$-alkyl, $C_3$–$C_6$-alkenyl, $C_3$–$C_6$-alkynyl, $C_3$–$C_8$-cycloalkyl, it being possible for these alkyl, cycloalkyl, alkenyl and alkynyl groups each to carry one to five halogen atoms, and/or one or two of the following groups:

$C_1$–$C_4$-alkyl, $C_1$–$C_4$-alkoxy, $C_1$–$C_4$-alkylthio, $C_1$–$C_4$-haloalkoxy, $C_3$–$C_6$-alkenyloxy, $C_3$–$C_6$-alkenlthio, $C_3$–$C_6$-alkynyloxy, $C_3$–$C_6$-alkynylthio, $C_1$–$C_4$-alkylcarbonyl, $C_1$–$C_4$-alkoxycarbonyl, $C_3$–$C_6$-alkenylcarbonyl, $C_3$–$C_6$-alkynylcarbonyl, $C_3$–$C_6$-alkenyloxycarbonyl and $C_3$–$C_6$-alkynyloxycarbonyl, phenyl, unsubstituted or substituted one or more times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, di-$C_1$–$C_4$-alkylamino, $R^7$ and $R^8$ are furthermore phenyl which is unsubstituted or substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $R^7$ and $R^8$ together form a $C_4$–$C_7$-alkylene chain which is closed to form a ring and may contain a hetero atom selected from the group of oxygen, sulfur or nitrogen;

b) a group

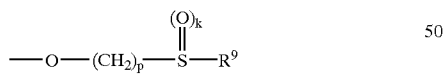

in which k assumes the values 0, 1 and 2, p assumes the values 1, 2, 3 and 4, and
$R^9$ is $C_1$–$C_4$-alkyl, $C_1$–$C_4$-haloalkyl, $C_3$–$C_6$-alkenyl, $C_3$–$C_6$-alkynyl or phenyl which is unsubstituted or substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

c) a radical —$OR^{10}$ where $R^{10}$ is:
hydrogen, an ammonium ion, the cation of an alkali metal, the cation of an alkaline earth metal or a tertiary $C_1$–$C_4$-alkyl ammonium;
$C_3$–$C_8$-cycloalkyl, which can carry one to three $C_1$–$C_4$-alkyl groups;
$C_1$–$C_8$-alkyl which can carry one to five halogen atoms and/or one of the following radicals:
$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, phenoxy or phenylcarbonyl, it being possible for the aromatic radicals in turn each to carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio; a $C_1$–$C_8$-alkyl group which can carry one to five halogen atoms and carries a 5-membered heteroaromatic system consisting of one to three nitrogen atoms and two to four carbon atoms, or a 5-membered heteroaromatic system consisting of one nitrogen atom, one oxygen or sulfur atom, and three carbon atoms wherein said 5-membered heteroaromatic system consisting of one to three nitrogen atoms and two to four carbon atoms can carry one to four halogen atoms and/or one or two of the following radicals: nitro, cyano, $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio;

a $C_2$–$C_6$-alkyl group which carries in position 2 one of the following radicals: $C_1$–$C_4$-alkoxyimino, $C_3$–$C_6$-alkynyloxyimino, $C_3$–$C_6$-haloalkenyloxyimino or benzyloxyimino;

a $C_3$–$C_6$-alkenyl or a $C_3$–$C_6$-alkynyl group, it being possible for these groups in turn to carry one to five halogen atoms;

$R^{10}$ is furthermore a phenyl radical which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio; a 5-membered heteroaromatic system which is linked via a nitrogen atom and consists of one to three nitrogen atoms and which can carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy or $C_1$–$C_4$-alkylthio;

$R^{10}$ is furthermore a group

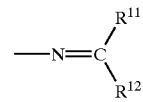

where $R^{11}$ and $R^{12}$, which can be identical or different, are:
$C_1$–$C_8$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or a phenyl radical which is unsubstituted or substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl which is unsubstituted or substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $R^{11}$ and $R^{12}$ together form a $C_3$–$C_{12}$-alkylene chain which may carry one to three $C_1$–$C_4$-alkyl groups and optionally contains a hetero atom from the group of oxygen, sulfur and nitrogen;

d) a radical

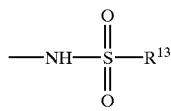

where $R^{13}$ is:

$C_1$–$C_4$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy-, $C_1$–$C_4$-alkylthio- and/or phenyl radical; phenyl which is unsubstituted or substituted by one or more of the following: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or e) a radical

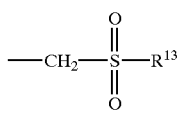

where $R^{13}$ has the abovementioned meaning;

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{14}$, where $R^{14}$ is hydrogen or $C_{1-5}$-alkyl, or $CR^{14}$ forms together with $CR^3$ a 5- or 6-membered alkylene or alkenylene ring which can be substituted by one or two $C_{1-4}$-alkyl groups and in which in each case one methylene group can be replaced by oxygen, sulfur, —NH or —N$C_{1-4}$-alkyl;

$R^3$ is halogen, $C_1$–$C_4$-alkyl, $C_1$–$C_4$-haloalkyl, $C_1$–$C_4$-alkoxy, $C_1$–$C_4$-haloalkoxy, —NH—O—$C_{1-4}$-alkyl, $C_1$–$C_4$-alkylthio or $CR^3$ is linked to $CR^{14}$ as indicated above to form a 5- or 6-membered ring;

$R^4$ and $R^5$, which may be identical or different, are:
phenyl or naphthyl, each of which can be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino, $C_1$–$C_4$-alkylamino or $C_1$–$C_4$-dialkylamino; or phenyl or naphthyl which are connected together in ortho positions by a direct linkage, a methylene, ethylene or ethenylene group, an oxygen or sulfur atom or SO$_2$, NH or N-alkyl group, or $C_3$–$C_7$-cyloalkyl;

$R^6$ is $C_1$–$C_{10}$-alkyl, $C_3$–$C_{10}$-alkenyl or $C_3$–$C_{10}$-alkynyl, the radicals each being substituted one or more times by hydroxyl, mercapto, carboxyl, sulfonyl, guanidino, or

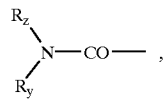

where $R_y$ and $R_z$ are, independently of one another, hydrogen or $C_1$–$C_5$-alkyl; and Z is sulfur or oxygen.

2. A compound as claimed in claim 1, wherein R is COOH.

3. A compound as claimed in claim 1, wherein at least one of the radicals $R^4$ and $R^5$ is phenyl.

4. A compound as claimed in claim 1, wherein $R^4$ and $R^5$ are both phenyl.

5. A compound as claimed in claim 1, wherein $R^6$ is $C_1$–$C_8$-alkyl, substituted by OH or $C_1$–$C_4$-alkoxy, and Z is O.

6. A compound as claimed in claim 1, wherein X is CH.

7. A compound as claimed in claim 1, wherein at least one of the radicals $R^2$, $R^3$ is $C_1$–$C_4$-alkyl.

8. A method of treating hypertension, which method comprises administering to a patient in need of such treatment an effective amount of the compound of formula 1 as defined in claim 1.

9. A composition comprising the compound of formula I as defined in claim 1 and an inhibitor of the renin-angiotensin system.

10. A compound as claimed in claim 1, wherein $R^1$ is selected from a), b) c) or d) described therein.

11. A compound as claimed in claim 1, wherein $R^6$ is $C_1$–$C_4$-alkyl or $C_3$–$C_5$-alkenyl, the radicals each being substituted once or twice by hydroxyl, mercapto or carboxyl.

12. A compound as claimed in claim 1, wherein $R^6$ is $C_1$–$C_4$-alkyl or $C_3$–$C_5$-alkenyl, the radicals each being substituted once or twice by hydroxyl or substituted once by carboxyl.

13. A compound as claimed in claim 1, wherein R6 is $C_1$–$C_3$-alkyl or $C_3$–$C_4$-alkenyl, the radicals each being substituted once or twice by hydroxyl or substituted once by carboxyl.

14. A compound as claimed in claim 1, wherein Z is O.

15. A compound as claimed in claim 12, wherein Z is O.

* * * * *